US00PP21196P3

(12) United States Plant Patent
Schräder

(10) Patent No.: US PP21,196 P3
(45) Date of Patent: Aug. 10, 2010

(54) **VARIETY OF *CUPHEA* PLANT NAMED 'VIEBURG'**

(50) Latin Name: *Cuphea llavea*
Varietal Denomination: Vieburg

(75) Inventor: Ralf Schräder, Lüdinghausen (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 171 days.

(21) Appl. No.: 12/283,767

(22) Filed: Sep. 16, 2008

(65) Prior Publication Data

US 2010/0071105 P1 Mar. 18, 2010

(51) Int. Cl.
*A01H 5/00* (2006.01)

(52) U.S. Cl. ..... Plt./420

(58) Field of Classification Search ..... Plt./420
See application file for complete search history.

*Primary Examiner*—Annette H Para
(74) *Attorney, Agent, or Firm*—The Webb Law Firm

(57) ABSTRACT

A new and distinct *Cuphea llavea* plant named 'Vieburg' with large, reddish-purple bicolored flowers and an upright growth habit.

2 Drawing Sheets

Botanical classification: *Cuphea llavea.*
Varietal denomination: 'Vieburg'.

BACKGROUND OF THE INVENTION

The present invention comprises a new and distinct cultivar of *Cuphea llavea* known by the varietal name 'Vieburg'. The new variety was discovered in 's Gravenzande, The Netherlands on Jul. 7, 2006. The new variety has been asexually reproduced via tip cuttings and the first date of asexual reproduction was Aug. 15, 2006 in 's Gravenzande, The Netherlands. The new variety is the result of a planned breeding program cross between unpatented *Cuphea llavea* plant Seedling C8 (female parent) and unpatented *Cuphea llavea* plant Seedling C5-2 (male parent). The purpose of the breeding program was to develop new varieties with bigger flowers and a broad range of color. The new variety exhibits strong growth and an upright habit that are similar to both parents, but does have a bigger flowers and an improved flower color when compared to both parents. 'Vieburg' exhibits similar vigor to *Cuphea llavea* 'Tiny Winie' (unpatented and also known as 'Torpedo'), but has bigger flowers, different flower color and more upright growth than 'Tiny Winie'. The new variety has been trial and field tested and has been found to retain its distinctive characteristics and remain true to type through successive propagations. The following characteristics distinguish 'Vieburg' from other *Cuphea llavea* varieties known to the breeder:

1. Large flowers;
2. Bicolored flowers; and
3. Improved upright growth.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
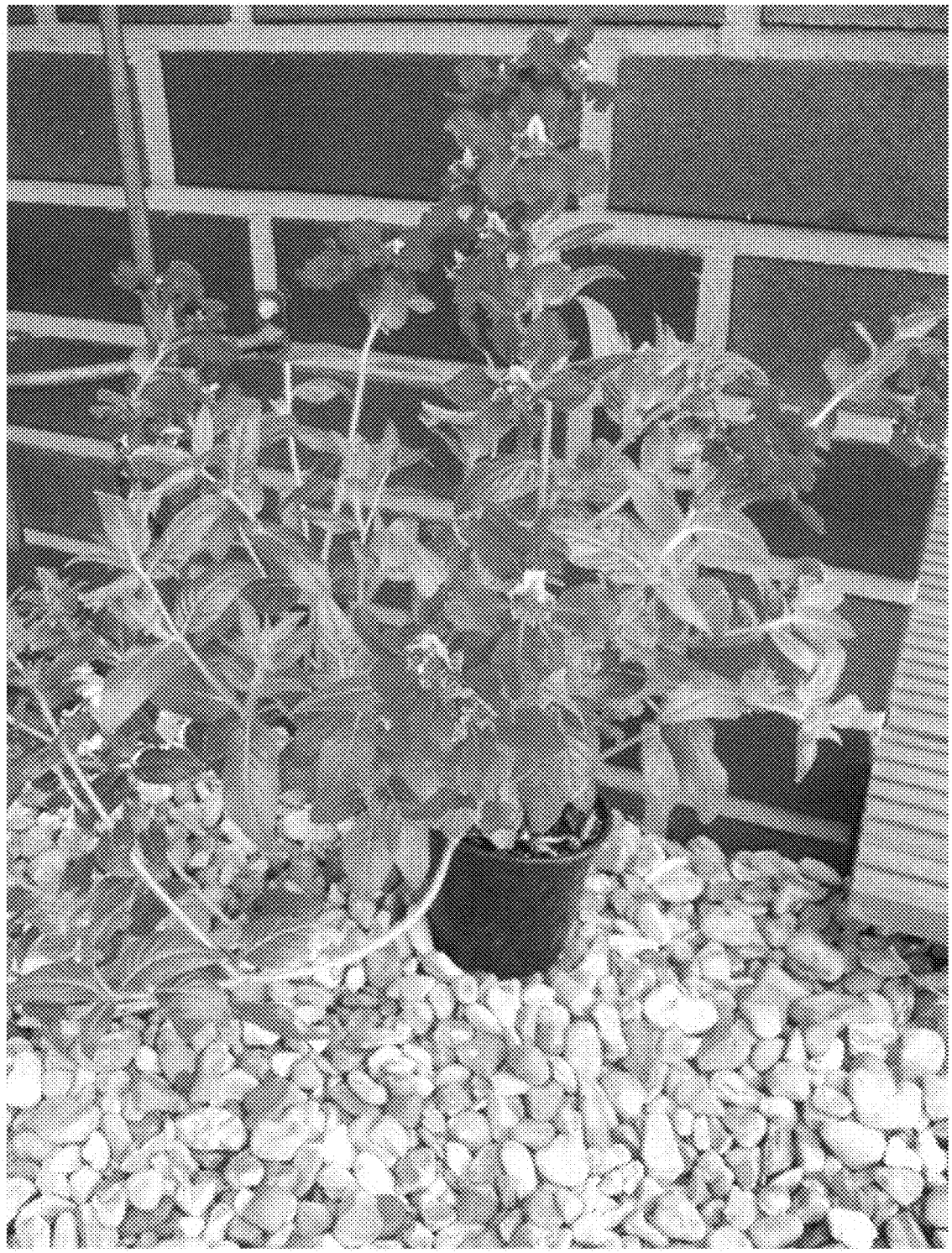
FIG. 1 is a view of an entire plant of the new variety.
Figure 2:
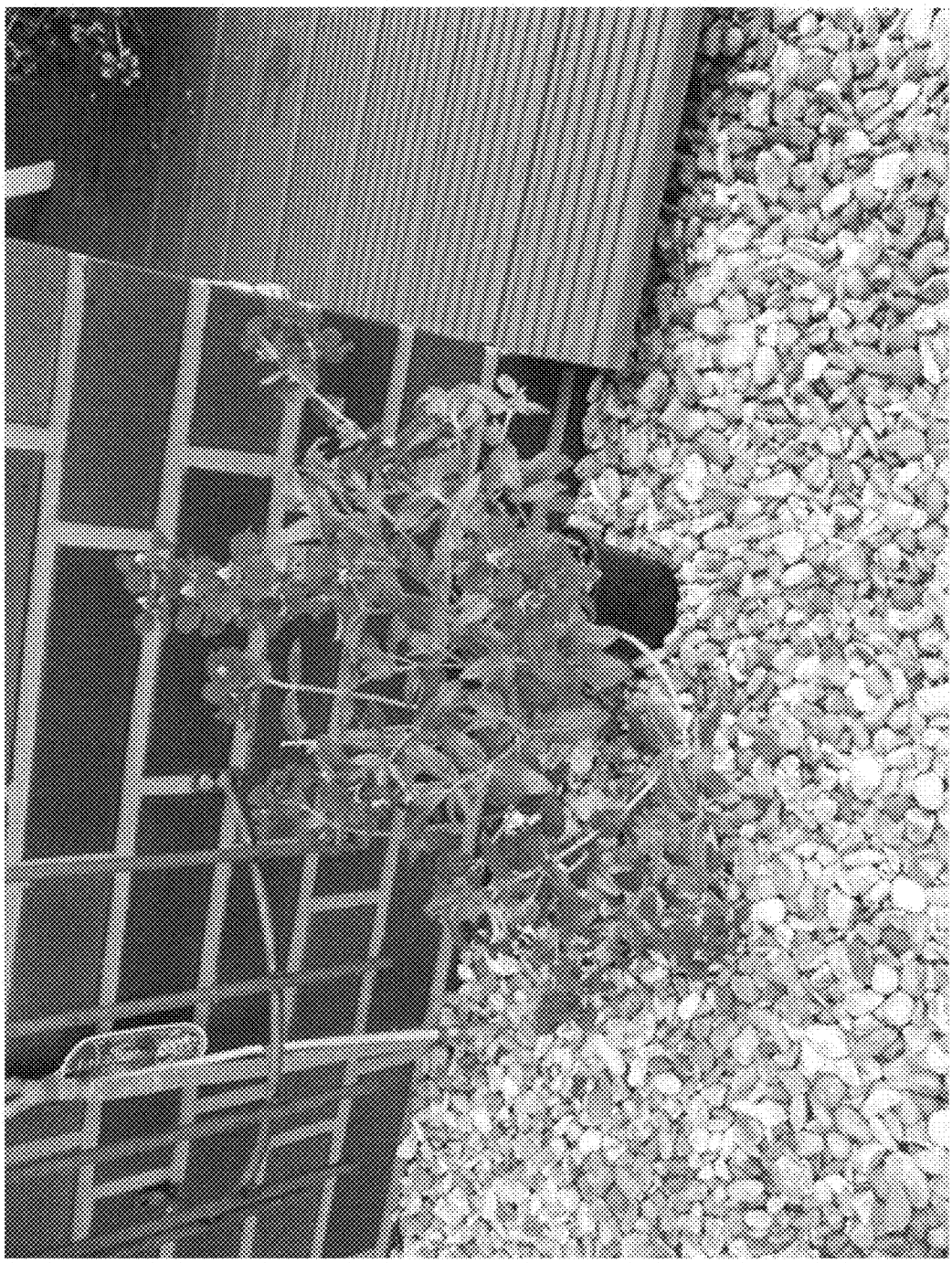
FIG. 2 is an additional photograph of an entire plant of the new variety.

The following detailed description sets forth the characteristics of a 10 week old 'Vieburg' plant grown inside a greenhouse in a 12 cm container in The Netherlands. The color readings were taken indoors under natural light. Color references are primarily to the R.H.S. Colour Chart of The Royal Horticultural Society of London.

PLANT

Time to initiate roots: About 12 days at about 18° C.
Time to develop roots: About 16 days at about 18° C.
Time to produce a finished flowering plant from a rooted cutting: About 10 weeks in a 12 cm container.
Rooting habit: Good, spreading.
Form: Spreading.
Branching habit: Upright.
Height: 35–40 cm.
Plant diameter: 15 cm.
Vigor: Strong.
Branching habit: Spreading upright, not much branching.
Lateral branches:
- *Length.*—18–24 cm.
- *Diameter.*—2.5–3 mm.
- *Internode length.*—4–6 cm.
- *Texture.*—Smooth and hairy.
- *Color.*—145C.

Foliage:
- *Arrangement.*—Alternate.
- *Number per branch.*—6–8.
- *Size of leaf.*—Length: 5.5–6 cm. Width: 2.5–2.7 cm.
- *Shape of leaf.*—Oval.
- *Shape of apex.*—Acute.
- *Shape of base.*—Round.
- *Texture.*—Smooth with some hairs.
- *Margin description.*—Glossy.
- *Color.*—Young leaves: Upper surface: 138A. Lower surface: 138B. Mature leaves: Upper surface: 137A. Lower surface: 138B to 138C.

*Petiole.*—Length: 14–16 mm. Diameter: 2.5–3 mm. Color: 139D.

*Veins.*—Venation type: Alternate. Color: Young leaves: Upper surface: 139D with N77A in the middle vein. Lower surface: 139D. Mature leaves: Upper surface: 138D with N77A in the middle vein. Lower surface: 139C to 139D.

FLOWER

Bud:

*Time of description.*—2 days before opening.

*Shape.*—Tube.

*Diameter.*—4–6 mm.

*Length.*—20–24 mm.

*Color.*—N170 with 185A hairs.

Natural flowering season: April–October in The Netherlands.

Flower type and habit: Single and lobed.

Number of flowers per lateral branch: 5–7.

Flower longevity on plant: 7–8 days.

Flower:

*Diameter.*—50×45 mm.

*Height.*—25–28 mm.

*Throat diameter.*—12 mm.

Corolla:

*Form.*—Actinomorphic; fused petals (lobed).

*Appearance.*—Open flower with a distance between the petals.

*Petals/lobes.*—Number: 6. Length: 15–18 mm. Width: 15 mm. Shape: Oval. Apex: Rounded. Base: Acuminate. Margin: Smooth. Texture and appearance: Very weak. Color: When opening: Upper surface: N60 and N79B to N79C. Lower surface: N60 and N79B to N79C. Fully opened: Upper surface: 60B and 79C. Lower surface: 60B and 79C.

*Throat.*—Color: 72B to 72C. Texture: Hairy.

*Tube color.*—N77A and N77B.

Calyx: No calyx or sepals present.

Fragrance: None.

Disease resistance: None observed to date.

Temperature tolerance: From 1° C. to 45° C.

REPRODUCTIVE ORGANS

Stamens:

*Number per flower.*—10.

*Filament length.*—6–10 mm.

*Anthers.*—Shape: Oval. Length: 1 mm. Color: 195B.

*Pollen.*—Color: 195B. Amount: Minimal.

Pistils:

*Length.*—20 mm.

*Styles.*—Length: 11 mm. Color: 196C.

*Stigma.*—Shape: Round. Color: 196C.

Seed production: Around 20–30.

I claim:

1. A new and distinct variety of *Cuphea llavea* plant named 'Vieburg' substantially as shown and described herein.

* * * * *